United States Patent
Nöcker et al.

(10) Patent No.: US 12,109,286 B2
(45) Date of Patent: *Oct. 8, 2024

(54) PROCESS FOR SEMIPERMANENT STRAIGHTENING AND PERMANENT SHAPING HAIR

(71) Applicant: KAO GERMANY GMBH, Darmstadt (DE)

(72) Inventors: Bernd Nöcker, Darmstadt (DE); Steven Breakspear, Darmstadt (DE); Peter Bauer, Darmstadt (DE); Manfred Dürr, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 589 days.

This patent is subject to a terminal disclaimer.

(21) Appl. No.: 15/757,894

(22) PCT Filed: Mar. 15, 2016

(86) PCT No.: PCT/EP2016/055581
§ 371 (c)(1),
(2) Date: Mar. 6, 2018

(87) PCT Pub. No.: WO2017/041903
PCT Pub. Date: Mar. 16, 2017

(65) Prior Publication Data
US 2020/0222292 A1    Jul. 16, 2020

(30) Foreign Application Priority Data
Sep. 8, 2015    (EP) .................................... 15184308

(51) Int. Cl.
| | |
|---|---|
| *A61K 8/362* | (2006.01) |
| *A61K 8/36* | (2006.01) |
| *A61K 8/41* | (2006.01) |
| *A61K 8/46* | (2006.01) |
| *A61K 8/73* | (2006.01) |
| *A61K 8/89* | (2006.01) |
| *A61Q 5/04* | (2006.01) |

(52) U.S. Cl.
CPC ............... *A61K 8/362* (2013.01); *A61K 8/36* (2013.01); *A61K 8/416* (2013.01); *A61K 8/46* (2013.01); *A61K 8/73* (2013.01); *A61K 8/89* (2013.01); *A61Q 5/04* (2013.01)

(58) Field of Classification Search
None
See application file for complete search history.

(56) References Cited

U.S. PATENT DOCUMENTS

| | | | |
|---|---|---|---|
| 3,533,417 A | 10/1970 | Bartoszewicz et al. | |
| 4,774,075 A | 9/1988 | Lang et al. | |
| 5,338,540 A * | 8/1994 | Lee | A61K 8/8182 424/70.4 |
| 5,601,620 A * | 2/1997 | Ishikawa | A61K 8/891 8/581 |
| 8,349,025 B2 * | 1/2013 | Wood | A61Q 5/10 8/405 |
| 8,906,352 B2 | 12/2014 | Malle et al. | |
| 9,872,824 B2 | 1/2018 | Kadir | |
| 10,076,485 B2 | 9/2018 | Beumer | |
| 2007/0044252 A1 * | 3/2007 | Kravchenko | A61Q 5/065 8/405 |
| 2007/0141007 A1 * | 6/2007 | Glynn, Jr. | A61K 8/70 424/70.11 |
| 2012/0312317 A1 * | 12/2012 | Mannozzi | A61Q 5/04 132/206 |
| 2013/0118520 A1 | 5/2013 | Mannozzi | |
| 2014/0196741 A1 * | 7/2014 | Cabourg | A61Q 5/00 424/70.2 |
| 2015/0034119 A1 | 2/2015 | Pressly et al. | |
| 2015/0037270 A1 | 2/2015 | Pressly et al. | |
| 2015/0374604 A1 * | 12/2015 | Kadir | A61K 8/49 549/230 |

FOREIGN PATENT DOCUMENTS

| | | | |
|---|---|---|---|
| EP | 2644186 | * | 10/2013 |
| EP | 3228300 | * | 11/2015 |
| GB | 1416564 | * | 12/1975 |
| JP | S64 9919 A | | 1/1989 |
| KR | 10-2004-0098688 | | 6/2006 |
| WO | 2007/135299 A1 | | 11/2007 |
| WO | 2011/104282 A2 | | 9/2011 |
| WO | 2012/010351 A2 | | 1/2012 |
| WO | WO 2014/068101 | * | 5/2014 |
| WO | WO2014067702 | * | 5/2014 |
| WO | 2015/017768 A1 | | 2/2015 |
| WO | 2015/5086230 A1 | | 6/2015 |

OTHER PUBLICATIONS

International Search Report dated Apr. 14, 2016, mailed Apr. 22, 2016.
Milady's Standard Cosmetology Textbook, Chapter 20, Copyright 2011 Cengage Learning.

* cited by examiner

*Primary Examiner* — Tigabu Kassa
(74) *Attorney, Agent, or Firm* — Norris McLaughlin, P.A.

(57) ABSTRACT

The present invention relates to a process for semi-permanent straightening and permanent shaping hair, especially human hair, for improved and milder semi-permanent straightening and permanent shaping. It is found out that when commonly used permanent shaping reducing composition is mixed with another composition comprising predominantly carboxylic acids, the permanent shaping effect of the composition is improved, homogeneous shaping of hair fibers is achieved and natural cosmetic properties of hair is maintained and hair may be semi-permanently straightened before such process.

15 Claims, No Drawings

PROCESS FOR SEMIPERMANENT STRAIGHTENING AND PERMANENT SHAPING HAIR

This application is the U.S. National Stage of International Application No. PCT/EP2016/055581, filed Mar. 15, 2016, which claims foreign priority benefit under 35 U.S.C. § 119 of European Application No. 15184308.3 filed Sep. 8, 2015 the disclosures of which are incorporated herein by reference.

The present invention relates to a process for semi-permanent straightening and permanent shaping hair, especially human hair, for improved and milder semi-permanent straightening and permanent shaping.

Known methods of hair straightening are first of all classified as permanent and semi-permanent hair straightening methods. The permanent straightening method involves application of reducing agents and after breakage of the disulfide bonds and putting hair physically into the straight shape, the disulfide bonds are reformed by mildly oxidizing the hair (U.S. Pat. Nos. 4,774,075, 5,338,540). The semi-permanent methods involve the use of hair straightening irons on wet hair (WO2007135299, US2012/312317, US2013/118520). Recently, a new method has been made available based on application of an aqueous solution of glyoxylic acid in a strongly acidic pH range in combination with ironing the hair. Such a method delivers long lasting hair straightening. The details of the method are disclosed in various patent applications from Kao Corporation which are published as international applications such as WO 2011/104282, WO 2012/010351.

Permanent shaping of hair involves application of a strongly reductive composition onto hair and leaving it for a certain period of time, usually at elevated temperatures, in order to open up the disulfide bonds and rebuilding them in the preferred shape with an application of a mild oxidative composition. Since the process involves the use of strong reductive and oxidative compositions, the hair fiber itself is affected by such treatment and therefore it also loses certain natural properties such as its strength against breaking, its natural elasticity, its natural shine and natural soft feel upon touching.

Moreover, the to be permanently shaped hair is not always homogenous in its physicochemical status as it may be damaged due to previous chemical treatments such as dyeing and permanently shaping and/or environmental effects. This often leads to inhomogeneous permanent shaping performance and therefore often consumers' dissatisfaction. Especially when semi permanently straightened hair is treated with a reducing composition, the desired straightening results are not obtained in comparison to hair which had not undergone semi-permanent straightening before. This is even the case when the hair is semi-permanently straightened long before the treatment with reducing compositions. Therefore there is a great need for milder and more effective permanent shaping compositions which overcome one or more of the above mentioned problems.

Recently in a series of patent applications (US2015/0034119, US2015/0037270, WO2015/017768) methods are published which claim benefits of the combined use of a bismaleate based binding agent in hair chemical treatments such as oxidative hair dyeing, permanently shaping and bleaching for improving of hair structure. The publications are silent on the core of the present invention.

After a long research and careful considerations of the consumers' needs, the inventors of the present invention have unexpectedly found out that when commonly used permanent shaping reducing composition is mixed with another composition comprising predominantly carboxylic acids, the permanent shaping effect of the composition is improved, homogeneous shaping of hair fibers is achieved and natural cosmetic properties of hair is maintained and hair may be semi-permanently straightened before such a process. The semi-permanent straightening process may have been carried out days, weeks, months before the hair is treated with the reducing composition.

In case the semi-permanent straightened hair treated with glyoxylic acid is to be permanently shaped using reductive and oxidative compositions, the permanent shaping results are only satisfactory, if the reductive composition is not combined with an additional composition comprising the aforementioned carboxylic acids prior to application onto hair.

Therefore, the first object of the present invention is a process for semi-permanent straightening and permanent shaping hair, especially human hair, wherein the semi-permanent straightening comprises the steps of:
a. optionally washing the hair with a cleansing composition and towel drying,
b. applying to the hair a treatment composition A comprising at least one compound of the general structure and/or a hydrate thereof and/or a salt thereof

$$R\text{—}CO\text{—}R' \qquad \text{Formula (I)}$$

wherein R is selected from hydrogen, COOH, CN, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{10}$ cycloalkyl, optionally substituted $C_6$-$C_{10}$ aryl or a 5-10-membered, optionally substituted heteroaryl group, wherein the optional substituents of the alkyl group are selected from halogen, hydroxyl, amino and $C_1$-$C_4$ alkoxy, and the optional substituents of the other groups are selected from halogen, hydroxyl, amino, $C_1$-$C_4$ alkyl and $C_1$-$C_4$ alkoxy and R' is COOH or H and wherein the composition has a pH in the range of 1 to 4 when R' is COOH and in the range of 1 to 6 when R' is H, c. leaving the composition A on the hair for 1 min to 90 min,
d. optionally rinsing the hair,
e. drying the hair,
f. heating the hair to a temperature in the range of 130° C. to 230° C.,
g. optionally washing the hair with a cleansing composition, wherein the permanent shaping comprises the steps of:
h. optionally washing and/or shampooing the hair and towel drying,
i. optionally, putting hair under tension,
j. applying to the hair a ready to use composition obtained by mixing the compositions B and D, wherein the composition B is an aqueous composition comprising one or more reducing agents, one or more alkalizing agents and having a pH in the range from 6.0 to 12.0, wherein the composition D is a composition comprising:
1) one or more carboxylic acids having three or more carboxyl groups and/or their salts, and
2) one or more additional organic acid and/or their salts having one or two carboxyl groups,
at a total concentration of 10% to 100% by weight, calculated to the total of the composition D, wherein the ready-to-use composition has a pH in the range of 6 to 12 and comprises the acids and/or its salts at a total concentration in the range of 1.0% to 10.0% by weight, calculated to the total of the ready-to-use composition, k. leaving the composition on the hair for 1 min to 45 min,
l. rinsing off the hair with water,
m. optionally drying and heating the hair,
n. applying to the hair an aqueous composition C comprising one or more oxidizing agents, preferably hydrogen peroxide, and has a pH in the range from 1.5 to 5, and is left on the hair for a period from 1 min to 45 min,
o. releasing the tension from hair in case the hair is put under tension in step (i),
p. rinsing hair and optionally washing with a cleansing composition.

The second object is a kit for hair, especially human hair, comprising the compositions A, B, C and D as defined above.

The composition A comprises at least one compound of the general structure and/or a hydrate thereof and/or a salt thereof

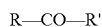  Formula (I)

wherein R is selected from hydrogen, COOH, CN, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{10}$ cycloalkyl, optionally substituted $C_6$-$C_{10}$ aryl or a 5-10-membered, optionally substituted heteroaryl group, wherein the optional substituents of the alkyl group are selected from halogen, hydroxyl, amino and $C_1$-$C_4$ alkoxy, and the optional substituents of the other groups are selected from halogen, hydroxyl, amino, $C_1$-$C_4$ alkyl and $C_1$-$C_4$ alkoxy, and R' is COOH or H.

The preferred compounds of Formula (I) are glyoxylic acid, pyruvic acid, 2-ketobutyric acid, and formaldehyde.

The compounds of Formula (I) may be comprised in the composition in its free acid form. The carbonyl group adjacent to the carboxyl group of the acid may also be present in the hydrate form. Apart from the free acid form and the hydrate thereof, salts of the acid or the hydrate may also be used.

The hydrate of the acid of Formula (I) may be formed when providing the composition as an aqueous solution. For instance, glyoxylic acid (H—CO—COOH) in aqueous solution is almost quantitatively present as the hydrate (H—C(OH)$_2$—COOH). Besides, the hydrate may also condense to dimers.

A salt of the carboxylic acid of Formula (I) may also be used. As examples, alkali metal salts such as the sodium or potassium salt, alkaline earth metal salts such as the magnesium salt or the calcium salt and ammonium salts may be mentioned.

In the present invention, glyoxylic acid is the most preferred carboxylic acid of Formula (I).

The concentration of the at least one compound of the formula (I) and/or a hydrate thereof and/or salts thereof is in the range of 0.1% to 40%, preferably 0.5% to 30%, more preferably 1% to 25% and even more preferably 2.5% to 20% by weight, calculated to the total of the composition A.

The pH of the composition A is in the range of 1 to 4.0 when R' is COOH, preferably in the range of 1 to 3, more preferably 1 to 2.5, as measured directly and at ambient temperature (25° C.), and in the range of 1 to 6 when R' is H. The pH of the compositions may be adjusted using known alkaline solutions, preferably with sodium hydroxide solution.

The semi-permanent straightening composition A of the present invention does not require the presence of sulfur-based reducing agents. However, up to 2% by weight calculated to the total of the composition sulfur based reducing agents does not interfere with the straightening performance of the compositions. Therefore, the treatment composition has less than 2% by weight of sulfur-based reducing agents, and preferably is free of sulfur-based reducing agents.

After application of the composition A it is left on the hair for a period of 1 min to 90 min and optionally rinsed off and the hair is optionally dried. Subsequently the hair is heated up to a temperature in the range of 130° C. to 230° C., using an iron, preferably a flat iron. When using the flat iron for heating the hair, the number of passages through the length of the hair may be determined depending on the degree of fizziness and/or curliness of hair. Typically, 2 to 8 passes through the hair should deliver a satisfactory straightening effect.

After completion of the semi-permanent straightening of the hair, the hair is washed and/or shampooed and put under tension, in case of curling on the curlers. Afterwards a reducing composition, composition B, is applied onto the hair after mixing with composition D (see below).

The composition B comprises one or more reducing agents. Useful are thiogylcolic acid and/or its salts, cysteamine and/or its salts, thioglycerin and/or its salts, glycerin esters of thioglycolic acid and/or its salts, thiolactic acid and/or its salts, cysteine or its derivatives and/or its salts and sodium sulfit. Preferred are thiogylcolic acid and/or its salts, thiolactic acid and/or its salts and cysteine or its derivatives and/or its salts. The most preferred is thiogylcolic acid and/or its salts.

One or more reducing agents are comprised in the composition B at a concentration in the range of 1% to 15%, preferably 2% to 15%, more preferably 3% to 12.5% and most preferably 5% to 11% by weight calculated to the total of composition B.

The composition B comprises one or more alkalizing agents. Suitable ones are ammonia and alkyl- or alkanolamines according to the general structure

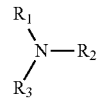

wherein $R_1$, $R_2$, and $R_3$ are same or different H, from $C_1$ to $C_4$, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_3$ to $C_4$ branched hydroxyl alkyl, with the condition that at least one of $R_1$, $R_2$, or $R_3$ is different from H, wherein the alkalizing agents preferably selected from ammonia, monoethanolamine, and aminomethyl-propanol, and particularly suitable one is aminomethyl-propanol.

The alkalizing agent is comprised in the composition B at a total concentration of 1% to 20%, preferably 1% to 17.5%, more preferably 2% to 15% and most preferably 2.5% to 13% by weight calculated to the total of the composition B.

The composition B has a pH in the range of 6 to 12, preferably 8 to 11, and more preferably 8 to 10.5 and most preferably 8.5 to 10 measured at 20° C.

The composition B is mixed prior to application onto hair with composition D.

The composition D comprises
1) one or more carboxylic acids having three or more carboxyl groups and/or their salts, and
2) one or more additional acids and/or their salts selected from inorganic acids and organic acids having one or two carboxyl groups.

Suitable carboxylic acids with three or more carboxyl groups and/or their salts are citric acid, ethylenediamine tetraacetic acid (EDTA), pyromellitic acid and glutamate diacetate. The ethylenediamine tetraacetic acid (EDTA) and/or its salts such a monosodium, disodium, trisodium and tetrasodium salts are the most preferred ones.

Suitable organic acids with one or two carboxyl groups and/or their salts are acetic acid, malic acid, lactic acid, glycolic acid, tartaric acid, formic acid, oxalic acid, malonic acid, succinic acid, glutaric acid, adipic acid, maleic acid, and fumaric acid. In the preferred embodiment of the present invention the composition D comprises as the second acid one or more organic acids having one or two carboxyl groups and the most preferred acid is malic acid and/or its salts such as sodium, potassium and ammonium salts.

The composition D comprises the two acids at a total concentration in the range of 10% to 100% by weight, preferably 12.5% to 90%, more preferably 12.5% to 75% by weight and most preferably 12.5% to 60% by weight, calculated to the total of composition D.

The two acids are comprised in the composition D at a weight ratio of first acid (1) to second acid (2) in the range from 10:1 to 1:250, preferably from 5:1 to 1:150, and more preferably from 2:1 to 1:100 and most preferably 1:50.

The composition D may be in the form of a powder, a dispersion, an emulsion or a solution. In a preferred embodiment of the present invention the composition D is an aqueous composition and preferably has a pH in the range of 1 to 5, preferably 2 to 4, more preferably in the range of 2.5 to 3.6. In the case that the pH must be adjusted to a certain value, the composition D comprises one or more alkalizing agents preferably selected from ammonia, alkyl- or alkanolamines according to the general structure disclosed above. Particularly preferred alkalizing agent is aminomethyl-propanol.

The alkalizing agent is comprised in the composition D at a total concentration of 1% to 20%, preferably 1% to 17.5%, more preferably 2% to 15% and most preferably 2.5% to 13% by weight calculated to the total of the composition D.

In a further preferred embodiment of the present invention, the composition D comprises one or more thickening polymers selected from anionic, nonionic, cationic and amphoteric polymers, preferably selected from polymers with a viscosity of at least 500 mPas measured at a polymer concentration of 1% by weight in water and at 20° C. with a Brookfield viscometer, such as at 10 rpm for 1 min, with an appropriate spindle.

Suitable polymers are cellulose polymers, alginates, polysaccharides and acrylic acid polymers, preferably methyl cellulose, ethyl cellulose, hydroxyethylcellulose, methylhydroxyethylcellulose, methylhydroxypropylcellulose, carboxymethyl cellulose, alginic acids, sodium alginates, ammonium alginates, calcium alginates, gum arabic, guar gum or xanthan gum, dehydroxanthan gum or acrylic acid polymers known with the CTFA adopted name Carbomer and its derivatives.

The preferred polymers are dehydroxanthan gum, xanthan gum, and polymeric anionic thickeners Carbomer and its derivatives. The particularly preferred thickening agent is dehydroxanthan gum. The thickening agents are preferably comprised in the composition D at a total concentration in the range of 0.1% to 5%, preferably, 0.2% to 3%, more preferably 0.25% to 2.5% and most preferably 0.3% to 2% by weight calculated to the total of the composition D.

The pH of the ready to use composition obtained by mixing the composition B and D, is in the range of 6.0 to 12, preferably 7.5 to 10.5, more preferably 7.8 to 10 measured at 20° C.

After leaving the mixture of the compositions B and D on the hair for a period of 1 min to 45 min, the hair is rinsed off with water and optionally dried and heated up.

Afterwards, an oxidizing composition, composition C is applied onto hair. The composition C is an aqueous composition and comprises one or more oxidizing agent(s). The oxidizing agents suitable are hydrogen peroxide, urea peroxide, melamin peroxide or perborate salts. The most preferred is hydrogen peroxide. The composition C comprises one or more oxidizing agents at a total concentration of 1% to 20% by weight, preferably 2% to 15%, more preferably 2% to 12% and most preferably 3% to 12% by weight, calculated to total of composition C. The composition B may be in the form of a solution, thickened gel or an emulsion. Emulsion form is particularly preferred.

pH of the composition C is in the range of 1.5 to 5, preferably 2.5 to 4.5, more preferably 2.5 to 4.

In the permanently shaping process an aqueous intermediate treatment composition may preferably be used in order to de-swell hair for minimizing further damage to the hair fibre after rinsing off the reducing composition. The intermediate composition is applied onto hair after rinsing off the reducing composition but before applying the oxidizing composition and preferably left on the hair up to 15 min, more preferably up to 10 min and optionally rinsed off from hair prior to application of oxidizing composition.

In principle any water soluble inorganic salt is suitable for the purpose. In the preferred embodiment, salts are preferably selected from salts of mono or divalent cations with mono and divalent anions. Preferred cations are sodium, calcium, potassium and magnesium and anions are chloride and sulfate. Suitable ones are such as sodium chloride, sodium sulfate, magnesium sulfate, potassium chloride, potassium sulfate, magnesium chloride, calcium chloride, ammonium salts such as ammonium chloride and ammonium sulfate. Additionally it has been found to be suitable especially salts of iodide ions especially potassium and sodium salts, copper chloride, copper sulphate, cobalt chloride, cerium sulphate, cerium chloride, vanadium sulphate, lithium chloride, magnesium acetate, calcium nitrate, barium nitrate, magnesium oxide, and ammonium nitrate. Preferred inorganic salts are sodium chloride, sodium sulfate, magnesium sulfate, potassium chloride, potassium sulfate, magnesium chloride, calcium chloride and salts of iodide ions. More preferably the salts are sodium chloride, sodium sulfate, magnesium sulfate, potassium chloride, potassium sulfate, magnesium chloride and salts of iodide ions especially potassium and sodium salts. In particular, with magnesium sulfate, sodium chloride and potassium iodide exceptionally good results are observed.

The total concentration of one or more inorganic salts in the aqueous intermediate composition is typically from 0.01% to 20%, preferably 0.05% to 15% and most preferably 0.1% to 10% and in particular 0.2% to 7.5% by weight calculated to the total of the intermediate composition.

The intermediate treatment composition may preferably comprise an oxidizing agent at a concentration of 0.1% to 5%, preferably 0.2% to 5% more preferably 0.2% to 3% and most preferably 0.2% to 2% by weight calculated to the total composition. Suitable oxidizing agents are hydrogen peroxide and sodium bromate. Most preferred is hydrogen peroxide.

The intermediate treatment composition has a pH between 2 and 7, preferably 2.5 and 6 and more preferably 3 and 5.

Although it is the preferred embodiment to carry out the semi-permanent straightening first and then permanent shaping one after another without any break, it is certainly possible to carry them out separately with a time delay of hours, even days, weeks and months. In another embodiment of the present invention, they may also be carried out in the reverse order if needed.

Any of the compositions A, B, C, and/or D may comprise one or more of the commonly used hair conditioning compounds. These compounds are for example fatty alcohols, surfactants such as anionic, nonionic, cationic and amphoteric ones, ubiquinones, ceramides, organic solvents, lipophilic ingredients such as vegetable oils, mineral oils, silicones, fatty acid fatty alcohol esters, preservatives, amino acids, and polyols. It should be noted that these compounds are optionally comprised in the any of the compositions and their incompatibility must be carefully considered prior to addition in the compositions.

Any of the compositions may comprise one or more fatty alcohols. In particular the compositions A, B, C, and/or D may be aqueous composition and may further be in the form of an emulsion and then comprises preferably one or more fatty alcohols.

Suitable fatty alcohols are the ones with the chain length of 14 to 22 C atoms which may be saturated or unsaturated, linear or branched which may as well be substituted. Non-limiting examples are myristyl alcohol, cetyl alcohol, steelyl alcohol, behenyl alcohol and cetostearyl alcohol.

The total concentration of fatty alcohol is in the range from 0.5% to 20%, preferably 1% to 15% by weight, calculated to the total of each composition.

Compositions according to the present invention may comprise surfactants selected from anionic, nonionic, amphoteric and/or cationic surfactants. The anionic, nonionic, amphoteric surfactants are used generally as emulsifier or solubilizer whereas the cationic surfactants are at the same time particularly used as hair conditioners. Anionic surfactants suitable are in principle known from the cleansing compositions. These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof as well as alkyl amido polyether carboxylic acids and salts thereof. Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfo-fatty acids and the esters thereof.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

It is also possible to use mixtures of several anionic surfactants.

Further suitable surfactants are nonionic surfactants. Non-limiting examples are long-chain fatty acid mono- and dialkanolamides, such as coco fatty acid mono- or diethanolamide and myristic fatty acid mono or diethanolamide, stearic acid mono or diethanolamide, alkyl polyglucosides with an alkyl group of 8 to 18 carbon atoms, and with 1 to 5 glucoside units, sorbitan esters, such as polyethylene glycol sorbitan stearic, palmitic, myristic and lauric acid esters, fatty acid polyglycol esters or poly-condensates of ethyleneoxide and propyleneoxide, as they are on the market, for example, under the trade name "Pluronics®", as well as fatty alcohol ethoxylates, $C_{10}$-$C_{22}$-fatty alcohol ethoxylates, known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2.5 and about 100, preferably about 10 and about 30.

Suitable amphoteric surfactants are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also been proven suitable.

Suitable cationic surfactants are according to the general structure

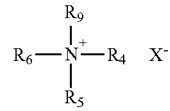

where $R_5$ is a saturated or unsaturated, branched or linear alkyl chain with 8-22 C atoms or

where $R_7$ is saturated or unsaturated, branched or linear alkyl chain with 7-21 C atoms and n has typical value of 1-4 or

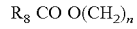

where $R_8$ is saturated or unsaturated, branched or linear alkyl chain with 7-21 C atoms and n has typical value of 1-4, and R$_4$ is H or unsaturated or saturated, branched or linear alkyl chain with 1-22 C atoms or R$_7$ CO NH(CH$_2$)$_n$ or R$_8$ CO O(CH$_2$)$_n$ where R$_7$, R$_8$ and n are same as above.

R$_9$ and R$_6$ are H or lower alkyl chain with 1 to 4 Carbon atoms, and X is typically chloride, bromide, methosulfate.

Typical examples of those ingredients are cetyl trimethyl ammonium chloride, stearyl trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

The concentration of one or more total surfactants in any of the compositions A, B, C, and/or D is in the range of 0.1% to 20%, preferably 0.2% to 15% and most preferably 0.2% to 10% by weight, calculated to the total of each composition.

The compositions A, B, C, and/or D may further comprise lipophilic ingredients such as vegetable oils, for example, jojoba oil or any other; liquid paraffins, especially paraffinum perliquidum and parafiinum subliquidurn, silicones for example linear polysiloxanes such as dimethicones with various consistency and dimethiconols, aminated silicones with primary, secondary, tertiary or quaternary ammonium groups such as amodimethicone, polysilicone 9, and quaternium 80, cyclic silicones such as cyclomethicones, arylated silicones such as phenyl trimethicone; fatty acid esters such as octyl palmitate, isocetyl palmitate, isopropyl palmitate and octyl stearate, C$_{10}$- to C$_{36}$-fatty acid triglycerides, as well as their mixtures. Total concentration of these lipophilic compounds is in the range of 0.1% to 20% by weight, preferably from 1% to 15% by weight, and more preferably from 2% to 10% by weight, calculated to the total of each composition.

Composition A, B, C, and/or D can also comprise cationic polymers as conditioning and/or thickening agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has been found suitable to use those cationic polymers known with their CTFA category name Polyquaternium. Typical examples of those Polyquaternium 4, Polyquaternium 6, Polyquaternium 7, Polyquaternium 10, Polyquaternium 11, Polyquaternium 16, Polyquaternium 22, Polyquaternium 24, Polyquaternium 28, Polyquaternium 30, Polyquaternium 37, Polyquaternium 36, Polyquaternium 46, Polyquaternium 67, and Polyquaternium 72.

Equally suitable polymers are known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

The total concentration of cationic polymers may be in the range of 0.1% to 7.5% by weight, preferably 0.3% to 5% by weight and more preferably 0.5% to 2.5% by weight, calculated to the total of each composition Compositions A, B, C, and/or D may comprise one or more ceramide compound, such as the one according to general formula

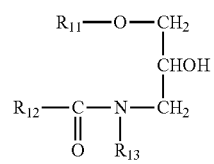

where R$_{11}$ and R$_{12}$ are independent from each other alkyl- or, alkenyl group with 10 to 22 carbon atoms, R$_{13}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide. Concentration of ceramide type of compounds ranges from 0.01% to 2%, preferably 0.01% to 1% by weight calculated to the total or each composition.

The compositions A, B, C, and/or D may comprise ubiquinone of the formula:

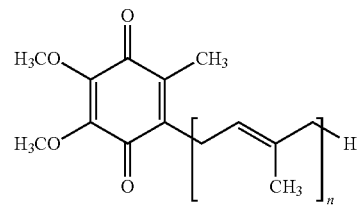

wherein n is a number from 1 to 10. The concentration of ubiquinone can vary between 0.001% and 10% by weight, calculated to the total of each composition.

The compositions A, B, C, and/or D may comprise one or more organic solvent such as 2-phenoxyethanol, benzyl alcohol, 2-phenylethanol and 2-benzyloxyethanol. Suitable aliphatic alcohols are ethanol, isopropanol, propanol, n-butanol, isobutanol, t-butanol and 1-pentanol. Concentration of one or more organic solvent is in the range of 0.1% to 15%, preferably 0.5% to 12.5% and more preferably 1% to 10% and most preferably 1% to 7.5% by weight calculated to the total of each composition.

The compositions A, B, C, and/or D may further comprise one or more amino acids, preferably at a concentration in the range of 0.01% to 5%, preferably 0.1% to 3% and more preferably 0.2% to 2.5% and most preferably 0.25% to 2% by weight calculated to the total of each composition. Suitable ones are all of the known amino acids such as, arginine, alanine, asparagine, glutamine, glycine, histidine, leucine, lysine, methionine, phenylalanine, proline, serine, threonine, tryptophan, tyrosine and valine.

The compositions A, B, C, and/or D may further comprise one or more polyols, preferably at a concentration in the range of 0.01% to 5%, preferably 0.1% to 3% and more preferably 0.2% to 2.5% and most preferably 0.25% to 2% by weight calculated to the total of each composition. Suitable ones are propylene glycol, diproplyene glycol, glycerine, panthenol and its derivatives.

The compositions A, B, C, and/or D may further comprise any known preservatives if necessary.

The following examples are to illustrate the invention, but not to limit it.

EXAMPLE 1

Composition A

|  | % by weight |
| --- | --- |
| Glyoxylic acid | 12.0 |
| Amodimethicone | 1.0 |
| Hydroxyethylcellulose | 1.5 |
| Sodium hydroxide | q.s. to pH 1.5 |
| Water | to 100 |

The Composition B

|  | % by weight |
| --- | --- |
| Ammonium thioglycolate (60%) | 21.3 |
| Ammonium hydrogen carbonate | 5.0 |
| 1,3- butylene gylcol | 3.0 |
| Amodimethicone | 0.2 |
| PEG-40-Hydrogenated castor oil | 0.7 |
| Fragrance | 0.4 |
| Ammonia, 25% | ad pH 8.3 |
| Water | ad 100.0 |

The Composition C

|  | % by weight |
| --- | --- |
| Hydrogen peroxide | 9.00 |
| Cetyl stearyl alcohol | 1.70 |
| Phosphoric acid | q.s. to pH 3.0 |
| Sodium lauryl sulfate | 0.20 |
| Salicylic acid | 0.10 |
| Water | ad 100.00 |

The Composition D

|  | % by weight |
| --- | --- |
| EDTA tetrasodium salt | 1.0 |
| Malic acid | 13.0 |
| Aminomethylpropanol | 6.0 |
| Hydroxypropyl xanthan gum | 0.6 |
| Cetrimonium chloride | 0.1 |
| Preservative | q.s. |
| Water | to 100 |

The pH of the above composition D was approximately 3.5.

Caucasian hair of 25 cm length was obtained from Fischbach+Miller, Laupheim, Germany. The composition A was applied to a shampooed and towel dried hair streak and left on the hair for 30 min at ambient temperature and the hair was dried with a hair drier. Afterwards the hair was treated with a flat iron having a surface temperature of 180° C. The streak was passed for 5 times with an iron. Then the hair was shampooed again and towel dried and put on curlers. Subsequently, the reducing composition B given above was applied onto hair after mixing with the composition D at a weight ratio of composition B to D 10:0.2 and processed for about 15 minutes. Then the composition was rinsed off from hair and an oxidizing composition C was applied and processed for about 10 minutes. The oxidizing composition was rinsed off and curlers were taken off from hair (inventive process).

For comparative purposes, the same as above was carried out without using the composition D in the permanent shaping part. Instead of composition D the same amount of water was added. The permanent shaping of the streaks was otherwise carried out exactly in the same way as describe above (comparative process).

Damage reduction was investigated on pre-damaged hair. Damage was conferred to hair by bleaching hair with a commercially available bleaching composition under the brand Goldwell. Then, the inventive and comparative processes of above were applied to separate hair streaks and processed as described above. Stress-strain analysis was conducted with the hair streaks upon these treatments on 30 hair fibers.

| | Comparative Process | | | | Inventive Process |
| --- | --- | --- | --- | --- | --- |
| Strain [%] | Virgin hair | Pre-damaged hair | Semi-permanent straightening | Permanent Straightening | Semipermanent and Permanent Straightening |
| | Stress [MPa] | | | | |
| 5 | 49.57 | 41.73 | 28.55 | 11.41 | 23.51 |
| 10 | 51.25 | 43.69 | 32.36 | 13.69 | 26.37 |
| 20 | 57.98 | 50.89 | 43.83 | 20.49 | 34.71 |
| 30 | 81.88 | 71.23 | 66.67 | 31.41 | 53.15 |
| 40 | 127.54 | 106.28 | 107.00 | 42.72 | 86.16 |

In the table of above lower stress values at a certain strain rate correspond to a higher amount of damage resulting in less elasticity of the hair fibers. The obtained data clearly showed that the hair streaks treated with a permanent straightening process had most damage compared to all other processes. The combination of semi-permanent straightening with permanent straightening was not possible with the comparative process because the hair was unusable for stress-strain analysis due to the severe damage. However, the inventive process made the combination of semi-permanent and permanent straightening available and in the end the treated hair streaks exhibited less damage compared to permanently shaped hair with the comparative process. This effect sustains over all investigated strain rates. Consequently the inventive process made the combination of semi-permanent and permanent shaping possible which was not the case with the to the state-of-the-art process.

Similar results were obtained with the following compositions (composition C and D) when used with the compositions of the Example 1.

EXAMPLE 2

The Composition D

| Component | % by weight |
| --- | --- |
| AMP | 6.0 |
| EDTA tetrasodium salt | 3.0 |
| Malic acid | 13.0 |
| Lactic acid | 4.0 |
| Hydroxypropyl xanthan gum | 0.6 |

-continued

| Component | % by weight |
|---|---|
| Polyquaternium-10 | 0.1 |
| Water | to 100 |
| pH | 3.4 ± 0.1 |

EXAMPLE 3

The Composition D

| Component | % by weight |
|---|---|
| Monoethanolamine (MEA) | 2.7 |
| EDTA tetrasodium salt | 5.0 |
| Malic acid | 15.0 |
| Hydroxypropyl xanthan gum | 0.6 |
| Panthenol | 0.1 |
| Water | To 100 |
| pH | 3.3 ± 0.1 |

EXAMPLE 4

The Composition D

| Component | % by weight |
|---|---|
| AMP | 6.0 |
| Citric acid | 5.0 |
| Maleic acid | 15.0 |
| Hydroxypropyl xanthan gum | 0.6 |
| Behenamidopropyl trimonium chloride | 0.2 |
| Water | to 100 |
| pH | 1.5 ± 0.1 |

EXAMPLE 5

The Composition D

| Component | % by weight |
|---|---|
| MEA | 2.0 |
| Lactic acid | 15.0 |
| Citric acid | 6.0 |
| Hydroxypropyl xanthan gum | 0.6 |
| Polyquaternium-67 | 0.1 |
| Water | to 100 |
| pH | 2.7 ± 0.1 |

EXAMPLE 6

The Composition D

| | % by weight |
|---|---|
| EDTA tetrasodium salt | 1.0 |
| Malic acid | 13.0 |
| Aminomethylpropanol | 6.0 |
| Hydroxypropyl xanthan gum | 0.6 |
| Cetrimonium chloride | 0.1 |
| Preservative | q.s. |
| Water | to 100 |

EXAMPLE 7

The Composition D (Powder)

| | % by weight |
|---|---|
| EDTA tetrasodium salt | 7.0 |
| Malic acid | 92.0 |
| Hydroxyethylcellulose | 1.0 |

1 g of the above composition D was added to the mixture of 100 g of composition B of the example 1. After mixing thoroughly, the resulting composition was applied onto semi-permanently straightened hair and it was observed that the hair was effectively curled and felt natural upon touching.

EXAMPLE 8

The Composition D

| | % by weight |
|---|---|
| EDTA monosodium salt | 1.0 |
| Malic acid | 13.0 |
| Aminomethylpropanol | 6.0 |
| Hydroxypropyl xanthan gum | 0.6 |
| Cetrimonium chloride | 0.1 |
| Preservative | q.s. |
| Water | to 100 | pH of the above composition D is approximately 3.1.

EXAMPLE 9

The Composition D

| | % by weight |
|---|---|
| EDTA disodium salt | 1.0 |
| Malic acid | 13.0 |
| Aminomethylpropanol | 6.0 |
| Hydroxypropyl xanthan gum | 0.6 |
| Cetrimonium chloride | 0.1 |
| Preservative | q.s. |
| Water | to 100 |

The pH of the above composition D is approximately 3.2.

EXAMPLE 10

The Composition D

| | % by weight |
|---|---|
| EDTA trisodium salt | 1.0 |
| Malic acid | 13.0 |
| Aminomethylpropanol | 6.0 |
| Hydroxypropyl xanthan gum | 0.6 |
| Cetrimonium chloride | 0.1 |
| Preservative | q.s. |
| Water | to 100 |

The pH of the above composition D is approximately 3.4.

EXAMPLE 11

The Composition A

| | % by weight |
|---|---|
| Glyoxylic acid | 10.0 |
| Amodimethicone | 1.0 |
| Hydroxyethylcellulose | 1.5 |
| Sodium hydroxide | q.s. to pH 1.5 |
| Water | to 100 |

The Composition B

| | % by weight |
|---|---|
| Ammonium thioglycolate (60%) | 21.3 |
| Ammonium hydrogen carbonate | 5.0 |
| 1,3- butylene gylcol | 3.0 |
| Amodimethicone | 0.2 |
| PEG-40-Hydrogenated castor oil | 0.7 |
| Fragrance | 0.4 |
| Ammonia, 25% | ad pH 8.3 |
| Water | ad 100.0 |

The Composition C

| | % by weight |
|---|---|
| Hydrogen peroxide | 2 |
| Phosphoric acid | q.s. to pH 3.5 |
| Water | to 100 |

The Composition D

| | % by weight |
|---|---|
| EDTA | 1.0 |
| Malic acid | 13.0 |
| Aminomethylpropanol | 6.0 |
| Hydroxypropyl xanthan gum | 0.6 |
| Cetrimonium chloride | 0.1 |
| Preservative | q.s. |
| Water | to 100 |

The composition D had a pH of 3.5.

A salon client with curly, oxidatively colored hair was subjected to a semi-permanent straightener treatment using the following steps:

treating the hair with a cleansing composition and the hair was towel dried,

Composition A was applied to the hair & left for 15 min before drying the hair with a hair-drier The hair was subsequently separated into sections & the individual sections were treated with 5 passes of a straightening iron set to 200° C.

The hair was washed with a cleansing composition & dried.

The clients' hair exhibited a homogeneous straightened result from root to tip

The same salon client returned after 4 months, with a regrowth of 5 cm which had been oxidatively colored (ie. the regrowth was oxidatively colored & curly while the hair treated 4 months before was oxidatively colored & wavy) & was subjected to a permanent straightening treatment using the following steps:

Hair is washed with a cleansing composition and towel dried,

Composition D & Composition B were mixed (mixing ratio 1:10) & the mixture was applied to the hair & left for 20 min before rinsing the hair with water & dried The hair was subsequently separated into sections & the individual sections were treated with 3 passes of a straightening iron set to 160° C.

Composition C was applied to the hair & left for 10 min before rinsing the hair with water.

The hair was washed with a cleansing composition & dried

The clients' hair exhibited a homogeneously straightened result from root to tip. For comparative purpose, an additional hair tress was permanently straightened as disclosed above, however Composition B was applied after mixing with water instead of with Composition D ((mixing ratio of water to composition B 1:10). It was observed that the tress showed a frizzy & kinky curl behavior & exhibited signs of damage when compared with the hair treated according to the invention.

The invention claimed is:

1. A process for semi-permanent straightening and permanent shaping hair,
   wherein the semi-permanent straightening hair comprises the steps of:
   a. washing the hair with a cleansing composition and towel drying,
   b. applying a first treatment composition A on the hair, wherein the first treatment composition A comprises glyoxylic acid, at least one hydrate of the glyoxylic acid, and/or at least one salt of the glyoxylic acid or the at least one hydrate of the glyoxylic acid,
   c. leaving the first treatment composition A on the hair for 1 min to 90 min,
   d. optionally rinsing the first treatment composition A off the hair,
   e. drying the hair,
   f. heating the hair to a temperature in the range of 130° C. to 230° C.,
   g. washing the hair with a cleansing composition and towel drying,
   wherein the permanent shaping hair is carried out after the semi-permanent straightening hair such that the first treatment composition A is applied onto the hair before a second ready-to-use composition and a third aqueous composition C are applied onto the hair and the permanent shaping hair comprises the steps of:
   h. optionally washing and/or shampooing the hair and towel drying,
   i. putting hair under tension,
   j. applying to the hair the second ready-to-use composition obtained by mixing a composition B and a composition D,
      wherein the composition B is an aqueous composition comprising one or more reducing agents and one or more alkalizing agents, the one or more reducing agents present at a concentration in the range of 2 to 15% by weight calculated to a total weight of composition B, and having a pH in the range from 8 to 11, measured at 20° C., wherein the composition D is a composition comprising:
1) ethylenediamine tetraacetic acid and/or its salts, and
2) malic acid and/or its salts,
wherein the ethylenediamine tetraacetic acid and/or its salts (1) and the malic acid and/or its salts (2) are present at a total concentration of 10% to 100% by weight, calculated to a total of the composition D and the composition D comprises the ethylenediamine tetraacetic acid and/or its salts (1) and the malic acid and/or its salts (2) at a weight ratio (1)/(2) in the range of 2:1 to 1:100,
wherein the second ready-to-use composition has a pH in the range of 6 to 12, measured at 20° C., and comprises the ethylenediamine tetraacetic acid and/or its salts (1) and the malic and/or its salts (2) at a total concentration in the range of 1.0% to 10.0% by weight, calculated to a total of the second ready-to-use composition,
k. leaving the second ready-to-use composition on the hair for 1 min to 45 min,
l. rinsing the second ready-to-use composition off the hair with water,
m. optionally drying and heating the hair,
n. applying the third aqueous composition C to the hair, wherein the third aqueous composition C comprises one or more oxidizing agents present at a total concentration of 1% to 20% by weight, calculated to a total weight of the third aqueous composition C, and having a pH in the range from 1.5 to 5, wherein the third aqueous composition C is left on the hair for a period from 1 min to 45 min,
o. releasing the tension from hair in case the hair is put under tension in step (i), and
p. rinsing hair and optionally washing with a cleansing composition.

2. The process according to claim 1 wherein the composition D is a powder, a dispersion, an emulsion or a solution and comprises the ethylenediamine tetraacetic acid and/or its salts (1) and the malic acid and/or its salts (2) at the weight ratio (1)/(2) in the range of 5:15 to 7:92.

3. The process according to claim 1 wherein the composition D is an aqueous composition.

4. The process according to claim 3 wherein the composition D has a pH in the range from 1 to 5, measured at 20° C.

5. The process according to claim 1 wherein the composition B comprises reducing agents from thiogylcolic acid, cysteamine and/or its salts, thioglycerin and/or its salts, glycerin esters of thioglycolic acid and/or its salts, thiolactic acid and/or its salts, cysteine or its derivatives and/or its salts, at a concentration in the range of 3 to 12.5% by weight, calculated to the total weight of composition B.

6. The process according to claim 1 wherein at least one alkalizing agent comprised in the composition(s) B and/or D is selected from ammonia, alkyl- or alkanolamines according to the general structure

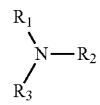

wherein R1, R2, and R3 are same or different H, from C1 to C4, C3 to C4 unsaturated alkyl, C3 to C4 branched alkyl, C1 to C4 hydroxyl alkyl, C3 to C4 unsaturated hydroxyl alkyl, C3 to C4 branched hydroxyl alkyl, with the condition that at least one of R1, R2, or R3 is different from H, wherein the at least one alkalizing agent is selected from ammonia, monoethanolamine, and aminomethyl-propanol.

7. The process according to claim 1 wherein the compositions A, B, C and/or D comprise one or more ingredients selected from selected from fatty alcohols, surfactants selected from anionic, nonionic, cationic and amphoteric ones, ubiquinones, ceramides, reducing agents, organic solvents, silicones such as linear polysiloxanes, aminated silicones, cyclic silicones, arylated silicones, antioxidants, preservatives, amino acids, polyols.

8. The process according to claim 1 wherein the semi-permanent straightening hair and permanent shaping hair steps are performed with a time delay of hours, days, week, or months therebetween.

9. The process according to claim 1 wherein the hair is heated with an iron.

10. The process according to claim 1 wherein the composition D comprises one or more thickening polymers selected from anionic, nonionic, cationic and amphoteric polymers, with a viscosity of at least 500 mPa·s measured at a polymer concentration of 1% by weight in water and at 20° C. with a Brookfield viscometer, at 10 rpm for 1 minute, with an appropriate spindle.

11. The process according to claim 10 wherein the thickening polymer is selected from hydroxypropyl xanthan gum, dehydroxanthan gum, xanthan gum, and polymeric anionic thickeners.

12. The process according to claim 1, wherein the one or more oxidizing agents are present at the total concentration of 2% to 15% by weight, calculated to the total weight of the third aqueous composition C.

13. The process according to claim 1, wherein the pH of the composition B is in the range of 8 to 10.5, measured at 20° C.

14. The process according to claim 1, wherein the pH of the second ready-to-use composition is in the range of 6.0 to 10.5, measured at 20° C.

15. The process according to claim 12, wherein the one or more oxidizing agents of the third aqueous composition C comprises hydrogen peroxide, urea peroxide, melamin peroxide or perborate salts.

* * * * *